United States Patent [19]
Alguire et al.

[11] 4,301,113
[45] Nov. 17, 1981

[54] CIRCULATION SYSTEM FOR BIOCIDAL GAS

[75] Inventors: Donald E. Alguire, Downers Grove; Robert Bennett, Chicago; Norbert Kotulla, Park Ridge; Anthony C. Yeung, Downers Grove, all of Ill.

[73] Assignee: Griffith Laboratories U.S.A., Inc., Alsip, Ill.

[21] Appl. No.: 184,248

[22] Filed: Sep. 5, 1980

[51] Int. Cl.³ .............................................. A61L 2/20
[52] U.S. Cl. ........................................ 422/2; 422/34; 422/117; 422/119; 422/292; 422/295
[58] Field of Search ................ 422/2, 31, 34, 32, 117, 422/119, 292, 295, 297

[56] References Cited

U.S. PATENT DOCUMENTS

| | | | |
|---|---|---|---|
| 3,238,096 | 3/1966 | Kaye | 422/34 X |
| 3,549,312 | 12/1970 | Ernst | 422/31 |
| 3,600,127 | 8/1971 | Kereluk et al. | 422/31 X |
| 3,897,210 | 7/1975 | Gruber et al. | 422/31 |
| 3,989,461 | 11/1976 | Skocypec et al. | 422/31 X |
| 4,130,393 | 12/1978 | Fox | 422/31 |

OTHER PUBLICATIONS

C. R. Phillips; "Gaseous Sterilization", presented 2/25/58 by B&D Co. & Seton Hall College of Med.

*Primary Examiner*—Barry Richman
*Attorney, Agent, or Firm*—Kegan, Kegan & Berkman

[57] ABSTRACT

In the treatment of articles with a sterilant gas such as an alkylene oxide, and the circulation of the gas throughout a treatment chamber containing the articles to be treated, a gas circulating system completely devoid of electrical contacts, switches, electrical motors and other potentially dangerous electrical components which could cause explosive ignition of the sterilant gas. The circulation system includes a fluid-driven turbine-like impeller completely isolated from the sterilant gas, and drivingly coupled to a fan blade which serves to force the gas through conduits and to circulate and recycle the sterilant gas throughout the treatment chamber. In a second embodiment of the invention a magnetically coupled drive is used to actuate the sterilant-circulating fan.

7 Claims, 2 Drawing Figures

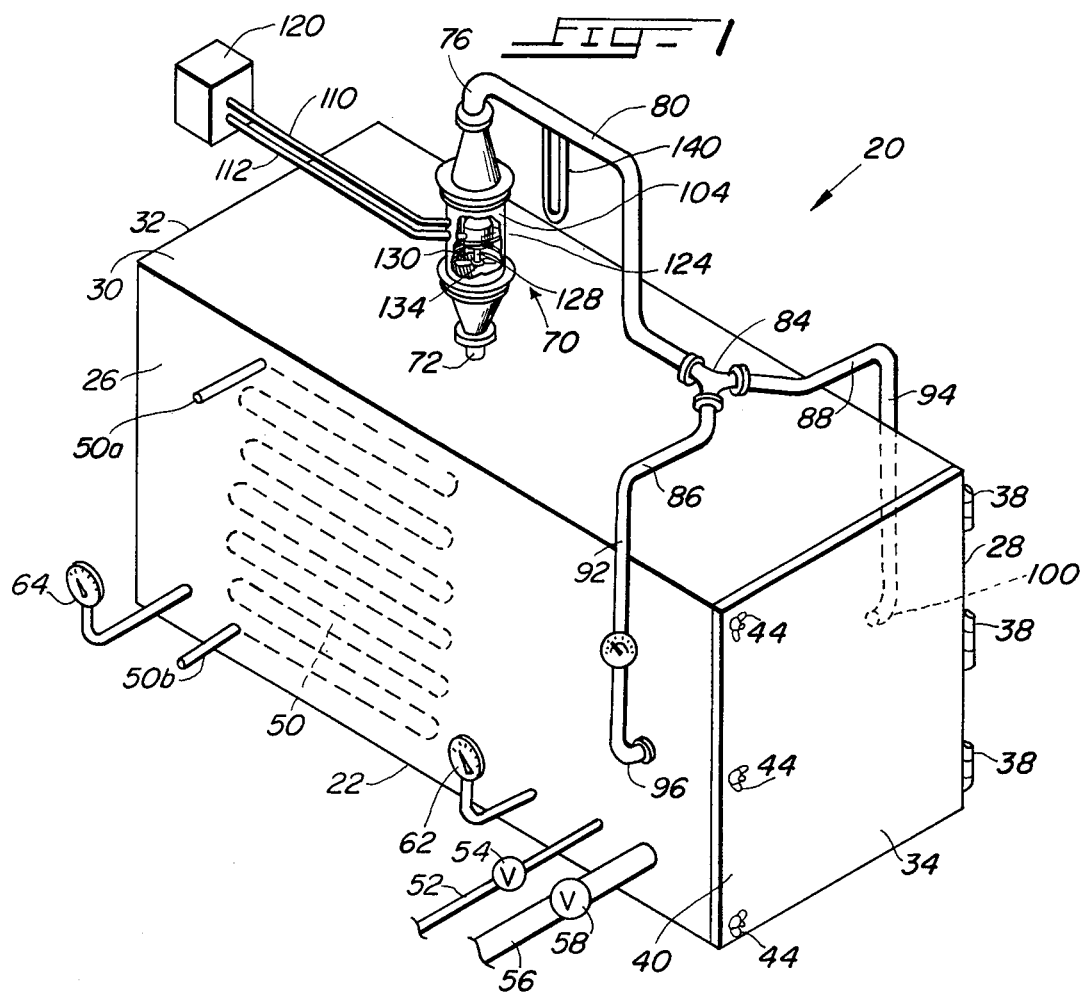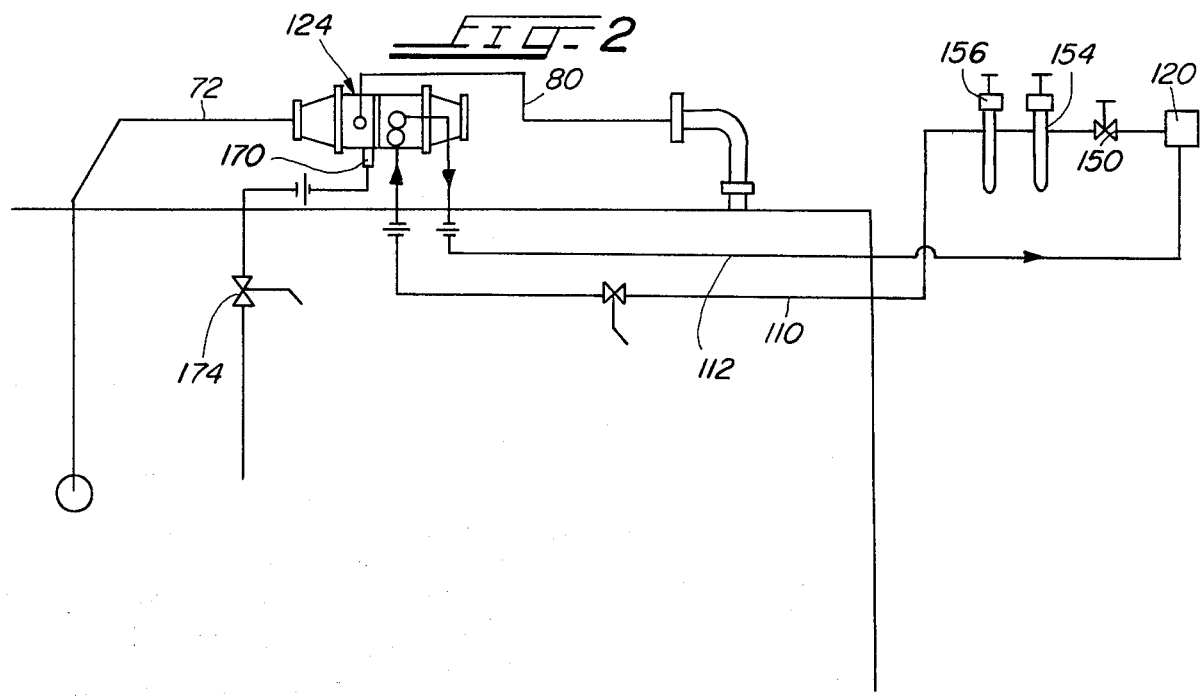

CIRCULATION SYSTEM FOR BIOCIDAL GAS

The present invention relates to a system for effectively circulating and distributing biocidal gas in and throughout a chamber containing articles which are to be treated to deactivate and to destroy viable microorganisms and insects, as well as life-cycle forms through which such organisms evolve. More particularly, the invention is directed to an explosion-proof and hazard-free circulation system by which the biocidal gas is distributed throughout and recycled through the treatment chamber containing the articles to be treated.

The present invention finds special utility when the sterilant gas used is an alkylene oxide such as ethylene oxide or propylene oxide. While these gaseous agents have many advantages such as being non-corrosive and being non-destructive with respect to sensitive and delicate articles including metals and other materials, as well as comestibles and drugs, the alkylene oxides have certain serious disadvantages in use. Specifically, they are highly flammable and are susceptible to explosive combustion, particularly in the presence of probable contaminants such as air.

Those skilled in the art have long recognized the hazards posed by these sterilant gases and have devised and adopted various procedures and techniques for minimizing such hazards. One widely used approach has been to dilute the alkylene oxide with an inert gas such as a halogenated hydrocarbon or with carbon dioxide to eliminate flammability and to prevent the development of explosive atmospheres.

Since the introduction of diluents into the alkylene oxide system has the undesirable effect of reducing the biocidal "activity" of the sterilant gas, there has been interest in devising apparatus and techniques which would enable one safely to use undiluted alkylene oxide. In site of extensive research and developmental work, no completely satisfactory alternative to dilution with an inert and fire-suppressing diluent has been found, and the general, widespread practice in the field has been to rely on such diluents to obviate the hazards of combustion and explosion.

It is, therefore, a principal aim of the present invention to provide a sterilant gas handling system including means for circulating such sterilant gas throughout a treatment chamber, all under condition which minimize and essentially obviate the type of hazards which have heretofore plagued the industry.

SUMMARY OF THE INVENTION

The present invention relates to apparatus and a method whereby the flammable and explosive alkylene oxide sterilant gases used as biocidal agents to reduce the bacterial count and otherwise to deactivate and destroy viable, objectionable organisms and other biological life may be safely, effectively and efficiently distributed and recycled through a reaction chamber under conditions in which the possibility of ignition or explosion of the biocidal gas is eliminated.

It is a principal feature of the invention that there is provided, in conjunction with a material treatment chamber into which a biocidal gas is introduced, gas circulation means which totally avoid and do not rely upon the presence of electrical equipment such as electrical motors, switches, contacts and the like, thereby to obviate any possibility of an electrical spark which might ignite the flammable biocidal gas.

It is a related feature of the invention that it renders it safe and practical to use "undiluted", essentially 100% active biocidal gases in a "sterilizing" process.

An important practical feature of the present invention is that the apparatus involved may readily be added to existing processing chambers without any substantial disruption or any requirement of major modification.

An important feature of the gas circulation system of the invention is that there is provided a fan or fan blade which is effectively isolated from the drive mechanism used to impart rotational movement to the fan.

Yet another feature of the invention is a fluid-driven turbine by means of which rotational movement is imparted to a gas circulating fan, the fluid input for driving the turbine and the turbne itself being isolated from any fluid communication with the treatment chamber in which the sterilant gas is circulated.

In a variant form of the invention, the sterilant gas circulating fan is caused to rotate by means of a magnetically coupled drive assembly.

A feature of the apparatus of the invention, in its various forms, is that it includes means for readily visually monitoring the rate in which the sterilant gas is circulated in the reaction vessel.

An important feature of the gas circulating apparatus of the invention is that it requires no modification of the internal structure of the reaction or treating chamber.

Yet another advantage of the invention is that the rate of gas circulation is continuously variable over a broad, selectible range.

A general, practical feature imparting valuable versatility to the invention is that the apparatus is essentially a self-contained, independent structure adapted conveniently for ready connection to and operation with existing gas sterilization installations to convert existing installations into systems in which undiluted alkylene oxides may be safely and effectively used.

Other and further objects, advantages, and features of the invention will become apparent from a consideration of the specifications in conjunction with the drawings.

DESCRIPTION OF THE DRAWING

FIG. 1 illustrates diagramatically a sterilizing chamber into which the gas circulation system of the invention, for distributing the sterilant gas throughout the chamber, has been incorporated; and FIG. 2 is a schematic representation of the apparatus and its controls for circulating the sterilant gas through the treatment chamber.

DESCRIPTION OF THE PREFERRED EMBODIMENTS

The aims and objects of the invention are achieved by attachment to a sterilizing chamber an assembly for circulating the biocidal gas throughout the chamber, and in which the impelling means for driving the fan blade of the circulation system is effectively isolated from the sterilant gas. The additional specific safety goals of the invention are achieved by using a circulating assembly which avoids the use of electrical motors, switches, controls or any other components which might give rise to objectionable sparks. Others of the objects and aims of the invention are achieved by providing a gas circulation system which may be part of a new "installation" or which, alternatively, may be added as a retrofit to existing installations.

Referring now to the drawings, and particularly, to FIG. 1, there is shown, for illustrative purposes and not in any limiting sense, a treatment chamber 20 of a generally elongated box-like configuration and having a floor 22, a pair of opposed sidewalls 26 and 28, a top 30, a rear-end wall 32 and a front wall 34. In the specific embodiment of the treatment vessel 20 illustrated, the front wall 34 is provided with lateral hinges 38 pivotally supporting the front wall 34 so that the latter may be swung to a fully open position. At its lateral end 40 opposite the hinges 38, the front wall 34 is provided with vertically spaced door-securement mechanisms 44. The structural material is preferably heavy guage steel, and the walls may be further stiffened and strengthened by means of channels, H-bars or similar reinforcements so that the chamber may be used either as a vacuum chamber or in hyperbaric applications.

In order further to enhance the versatility of the chamber 20, the latter is provided with heater means which, in the specific embodiment of the apparatus shown, comprise convoluted or sinuously arranged steam coils 50, provided with input and exhaust leads 50a and 50b, supported on the interior wall face of the chamber 20. The treatment vessel 20 is also provided with means to introduce various utilities, for example, a water or water vapor input line 52 and a control valve 54, a pipe 56 for the introduction and withdrawal of sterilant gas, and a control valve 58, a pressure sensor and indicator 62, and a thermometer 64.

Referring further to FIG. 1, the apparatus of the invention for circulating the sterilant gas is shown as comprising a turbine and fan assembly 70 one end 72 of which is piped into the chamber 20 through the top wall 30 and the other end 76 of which is connected to a generally horizontally extending gas conduit 80 which is branched at a T or Y 84 to provide a pair of generally symmetrical laterally extending arms 86 and 88 each being joined respectively to vertically extending pipe segments 92 and 94 extending downwardly on each of opposed sides 26 and 28 of the chamber 20. At their ends 96 and 100 opposed to the yoke 84, the pipe segments 92 and 94 are coupled through the side walls 26 and 28 of the chamber in fluid communication with the interior of the chamber 20.

Connected to the bounding wall 104 of the turbine housing are a fluid supply line 110 and a fluid return line 112, the lines constituting means by which pressurized fluid such as compressed air is forcibly delivered from a compressed air supply 120 to circulate through the turbine housing and to drive the turbine contained therein.

The turbine blade 124 is rotatably supported on a shaft 128 which extends through a fluid-tight bushing or seal 130. A fan blade 134 is mounted on the end of the shaft 128 and within a chamber of the gas circulating assembly 70 in communication with the interior of the treatment chamber 20 so that driven rotation of the turbine causes functional rotation of the fan blade 134 and movement of the gas through the treatment chamber 20 and the associated piping or conduit system.

In the particular embodiment of the invention illustrated, the direction of travel of the gas in the external pipe system 80, 84, 88, and 86 is from right to left. A flow meter 140 connected into the horizontal pipe 80 of the gas circulation system provides a visual indication of the gas flow rate through that system. As shown, the gas in the system circulates in a counterclockwise direction, gas being drawn from the reaction chamber at each of the forward lateral pipe connections 96 and 100 to flow upward and rearwardly through the parallelly disposed piping arms 86 and 88, through the T connector 84 and then in the trunkline 80 and to the circulator assembly 70. The circulating gas passes through the turbine driven circulator and is returned to the treatment chamber 20 at the top pipe connection 72.

FIG. 2 is a diagrammatic representation of the gas circulation system driven through a closed-loop compressed air line in which compressed air from an air supply unit 120 is fed through a valve 150 and then through an air filter 154, a lubricator 156, and an input line 110 to the turbine housing 70 to drive the turbine 124 and its associated shaft 128 and the fan blade 134 carried on that shaft, but isolated from the turbine housing. The forced air exits from the turbine chamber through a return conduit 112 to the air pump or compressor 120, to complete the closed-loop cycle. Alternatively, the return air could be discharged to atmosphere. In order to prevent the undesirable accumulation of fluid in the air circulation assembly 70, the latter is provided with a drain line 170 and a drain valve 174.

What is claimed is:

1. In the operation of a treatment chamber containing articles to be treated to reduce the concentration of viable micro-organisms and insects present in said articles as contaminants thereof and including the step of exposing said articles to a biocidal gas, said gas being further characterized by a high degree of flammability, the improvement comprising circulating said gas throughout said chamber to enhance contact between said gas and articles in said chamber while obviating possible inherent explosion and ignition hazards of said gas contained in said chamber, said improvement further comprising circulating said gas under conditions completely to isolate said gas from contact with electrical devices and circuitry, and including the steps of attaching to said chamber a gas circulation loop having spacially separated gas input and gas exhaust ports communicating with the interior of said chamber at remote locations therein, connecting fan means in said loop for circulating gas through said loop and through said chamber in fluid-flow communication therewith, operatively coupling turbine means to said fan means for forcibly rotating said fan means to circulate said gas, maintaining said turbine means in gas flow isolation from said fan means and from said gas circulation loop and said chamber, developing pressurized turbine driving fluid in a fluid-confining system isolated from said chamber and from said gas circulation loop, and delivering said pressurized fluid to impel said turbine means to impart rotational gas circulating movement to said fan means.

2. In a treatment chamber for the sterilization treatment of articles with a biocidal gaseous agent to reduce the concentration of viable organisms present as contaminants of said articles, and including means for introducing said gaseous agent into and means for removing said gaseous agent from said chamber, the improvement comprising gas circulating means for distributing and moving said gaseous agent throughout said chamber to enhance the effectiveness of the contacting of said gaseous agent to said articles contained in said chamber, and to obviate the possibility of igniting and exploding a combustible said gaseous agent contained in said chamber, said gas circulating means being characterized in that it is devoid of electrical circuitry and electrical components in contact with, adjacent to, and within said treatment chamber and acting upon said gaseous agent contained in said chamber, said gas circulating means including a fluid-tight housing, turbine means within said fluid-tight housing, said turbine means comprising fluid-driven motor means including vane means, shaft means mechanically coupled to said vane means in said turbine housing, said vane means being responsive to impingement of turbine-driving fluid directed forcibly thereagainst to effect rotation of said vane means and said shaft means coupled thereto, piping means connected to said turbine housing for delivery of turbine-driving fluid to said vane means of said turbine means, said gas circulating means for impelling said gaseous bocidal agent including fan means distinct from said turbine means and in fluid flow isolation therefrom, means coupling said fan blade means to said shaft means for driving rotation thereby, said gas circulating means having a gas inlet port and a gas exit port, conduit means connected at said gas inlet port and at said gas exit port, said conduit means being in circulatory gas flow communication with said treatment chamber, and including connector means coupling said conduit means into said treatment chamber at spacially separated zones thereof to enhance recycling circulation of said gaseous agent through said treatment chamber and through said articles contained therein, upon actuation of said turbine means and said gas impelling fan means driven thereby.

3. The apparatus as set forth in claim 2 and further comprising gas flow indicator means for visually monitoring the rate of gas flow through said conduit means of said gas circulating means.

4. The apparatus as set forth in claim 2 and further comprising trap means for separating liquid from the gas circulated through said treatment chamber and said conduit means.

5. The apparatus as set forth in claim 2 and further comprising valve means for controlling the rate of turbine driving fluid flow through said turbine means.

6. The apparatus as set forth in claim 2 and further comprising compressor means for forcibly circulating compressed air through said turbine means for driving said vane means to impart rotation to said fan means.

7. The apparatus as set forth in claim 6 and further comprising filter means for removing particulate foreign material from compressed air fed to said turbine means.

* * * * *